United States Patent [19]

Antranikian et al.

[11] Patent Number: 5,370,997
[45] Date of Patent: Dec. 6, 1994

[54] HYPERTHERMOSTABLE ALPHA-AMYLASE

[75] Inventors: Garabed Antranikian; Rainhard Koch; Andreas Spreinat, all of Göttingen, Germany

[73] Assignee: Novo Nordish A/S, Bagsvaerd, Denmark

[21] Appl. No.: 11,077

[22] PCT Filed: Mar. 19, 1990

[86] PCT No.: PCT/DK90/00074

§ 371 Date: Aug. 22, 1991

§ 102(e) Date: Aug. 22, 1991

[87] PCT Pub. No.: WO90/11352

PCT Pub. Date: Oct. 4, 1990

Related U.S. Application Data

[63] Continuation of Ser. No. 752,455, Aug. 22, 1991, abandoned.

[30] Foreign Application Priority Data

Mar. 20, 1989 [DE] Germany .............................. 3909096

[51] Int. Cl.$^5$ ...................... C12P 39/00; C12P 19/14; C12N 9/28; C12N 1/20
[52] U.S. Cl. ...................... 435/712; 435/42; 435/71.1; 435/99; 435/252.4; 435/275; 435/822; 435/202
[58] Field of Search ................ 435/202, 42, 99, 252.4, 435/822, 71.1, 71.2, 275

[56] References Cited

U.S. PATENT DOCUMENTS

| | | | |
|---|---|---|---|
| 4,316,956 | 2/1982 | Lutzen | 435/161 |
| 4,600,693 | 7/1986 | Kindle et al. | 435/176 |
| 4,628,031 | 12/1986 | Zeikus et al. | 435/205 |
| 4,717,662 | 1/1988 | Montgomery et al. | 435/99 |
| 4,734,365 | 3/1988 | Haga et al. | 435/99 |
| 4,778,760 | 10/1988 | Ishida et al. | 435/202 |
| 4,929,557 | 5/1990 | Antranikian et al. | 435/202 |
| 4,933,279 | 6/1990 | Carroll et al. | 435/202 |
| 5,188,956 | 2/1993 | Nanmori et al. | 435/200 |
| 5,242,817 | 9/1993 | Kelly et al. | 435/220 |

FOREIGN PATENT DOCUMENTS

| | | |
|---|---|---|
| 0258050 | 3/1988 | European Pat. Off. |
| 0268193 | 5/1988 | European Pat. Off. |
| 0276806 | 8/1988 | European Pat. Off. |

OTHER PUBLICATIONS

Plant et al., System. Appl. Microbiol., vol. 9, pp. 158–162 (1987).

*Primary Examiner*—Douglas W. Robinson
*Assistant Examiner*—Deborah K. Ware
*Attorney, Agent, or Firm*—Steve T. Zelson; Elias J. Lambiris

[57] ABSTRACT

A hyperthermostable alpha-amylase is provided by culturing strains of Pyococcus. These enzymes are of great interest for industrial applications, for example in starch liquefaction processes. The microorganisms *Pyococcus woesei* or *Pyococcus furiosus* are capable of producing the desired alpha-amylase with the following properties:

(a) a pH optimum between 4.0 and 6.0;
(b) a temperature optimum between 80 and 120 degrees centigrade;
(c) an activity which is essentially independent of calcium ions; and
(d) a residual activity of 100% after one hour at 90 degrees centigrade and of at least 80% after one hour at 100 degrees centigrade in the presence of stabilizing amounts of substrate.

10 Claims, 7 Drawing Sheets

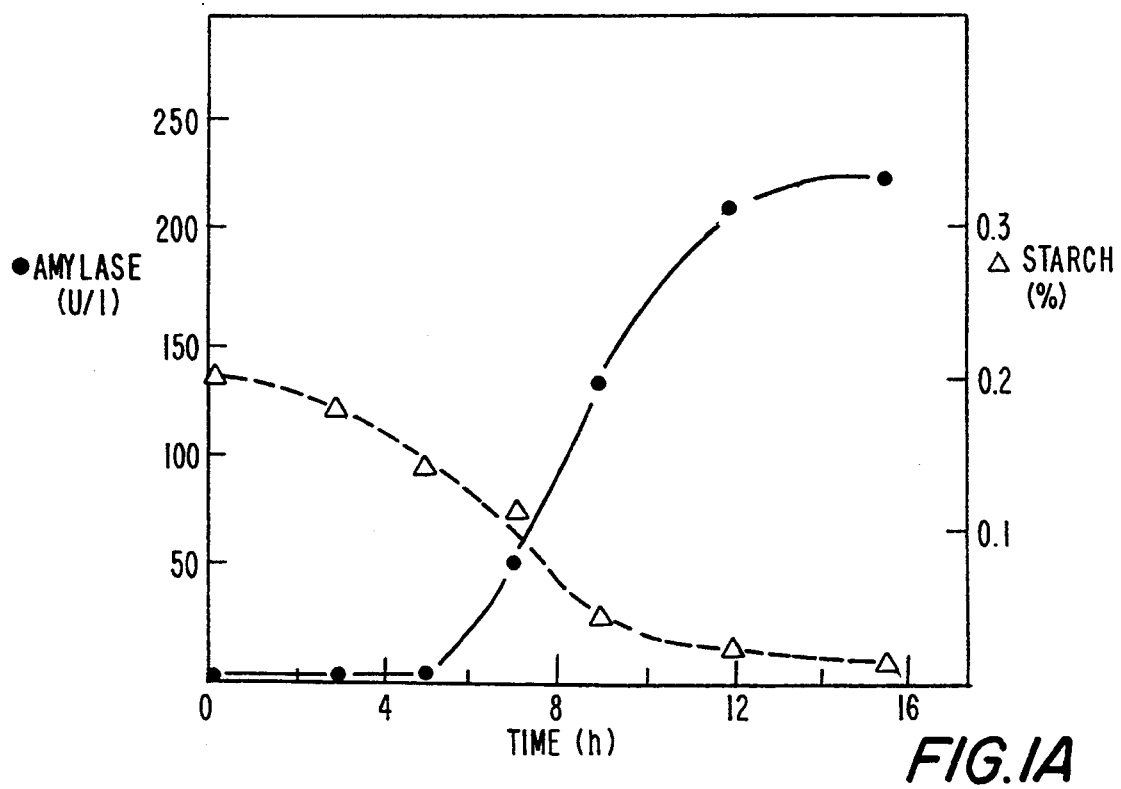
FIG.IA
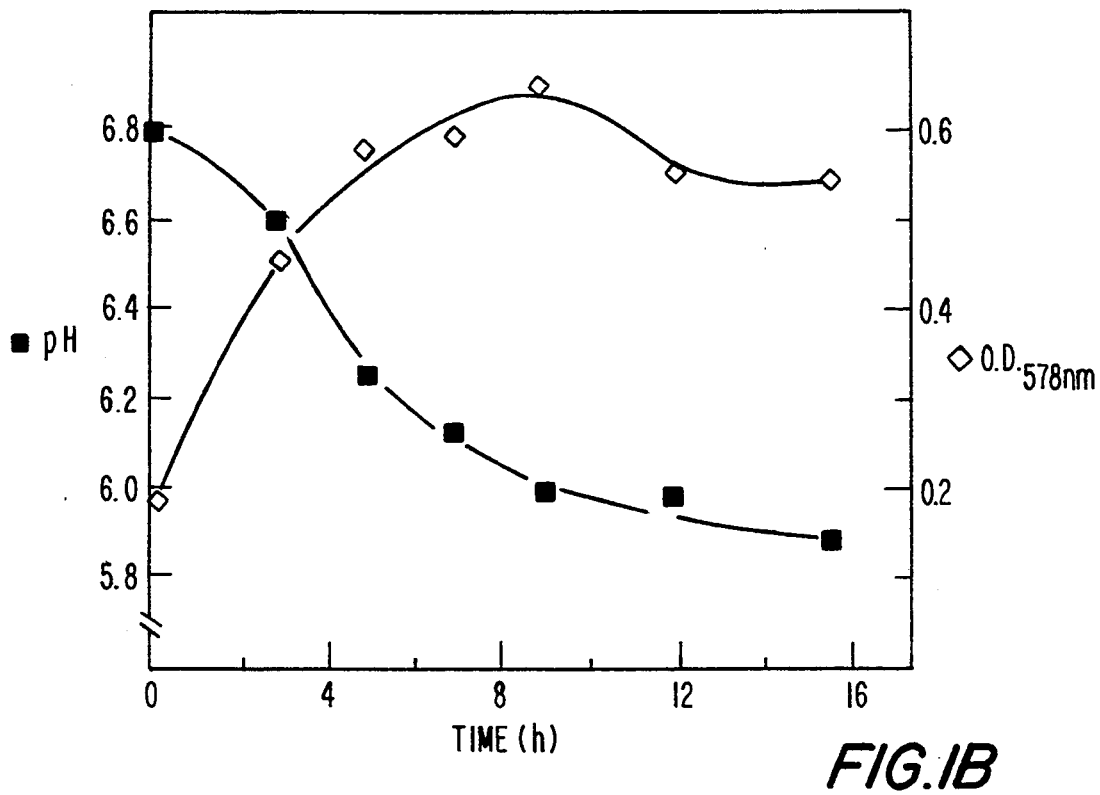
FIG.IB

HYPERTHERMOSTABLE ALPHA-AMYLASE

This application is a continuation application of application Ser. No. 07/752,455, filed Aug. 22, 1991, now abandoned.

TECHNICAL FIELD

This invention is within the field of thermostable α-amylases. More specifically, the present invention relates to novel hyperthermostable α-amylases, a process for the preparation of such enzymes and the use of these α-amylases in an industrial starch liquefaction processes.

BACKGROUND ART

The use of α-amylases for enzymatic conversion of starch into sugars, e.g. for the production of fuel alcohol or High Fructose Syrup (HFS), is widely practised. Among industrial starch liquefaction processes jet-cooking is the almost globally preferred mode of starch liquefaction, but for the performance of this process thermostable α-amylases are required.

HFS is manufactured from high DX syrups, the term DX meaning percentage by weight of dextrose (D-glucose) calculated on the basis of dry substance (DS) of syrup. The overall enzymatic liquefaction process generally adopted for conversion of starch into high DX syrup is a two-stage process. The first step is the liquefaction, i.e. the hydrolysis of starch into a mixture of oligosaccharides, the so-called maltodextrins. This process is catalyzed by α-amylases, and in a typical jet-cooking process the starch slurry is heated for at least several minutes to 105°–110° C., usually with a single dose of α-amylase, and then held at about 90° C. for at least 1 hour. In the primary stage of the overall liquefaction, gelatinization and mechanical thinning of the starch slurry are effected. Further degradation (dextrinization) occurs in the secondary stage of the process. With respect to the jet-cooking process, reference is made to U.S. Pat. No. 3,912,590.

Hitherto mostly preferred thermostable α-amylases for industrial liquefaction processes are of bacterial origin and from the genus Bacillus. Thus a well adapted α-amylase for use in the jet-cooking Process is TERMAMYL® from *Bacillus licheniformis*, supplied by NOVO NORDISK A/S, Denmark. α-amylases from *Bacillus stearothermophilus* are disclosed in U.S. Pat. Nos. 2,695,683 and 4,284,722. A *Bacillus stearothermophilus* α-amylase (THERMOLASE ™) is available from Enzyme Development Corporation, NY, USA.

Due to the Properties of the α-amylases hitherto available, the liquefaction process is typically performed at pH about 6.0–6.5. At pH below 6 the amylolytic activity rapidly decreases, and at pH above 6.5 the formation of unwanted byproducts such as maltulose or maltulose "precursors" become troublesome. *Bacillus licheniformis* α-amylase, for instance, is rapidly inactivated at pH values below 6.0. Moreover it requires at least 50 ppm calcium for stabilisation when used for industrial starch liquefaction, and it is completely inactivated at 120° C. The *Bacillus stearothermophilus* α-amylase has certain advantages over the *Bacillus lichenformis* enzyme, notably a lower pH optimum. However these enzymes are not fit for starch liquefaction at pH values below 5.

The subsequent saccharification step, in which the maltodextrins are converted into dextrose, is mostly catalyzed by a glucoamylase enzyme. Commercial glucoamylase preparations, usually derived from *Aspergillus* or *Rhizopus* species, are available from various manufacturers, e.g. as AMG ™ 200 L, a product obtained from *Aspergillus niger* and manufactured by NOVO NORDISK A/S, Denmark. These glucoamylase enzymes operate optimally at pH 4.0–4.5.

Now hyperthermophilic archaebacteria have been isolated from solfataric and submarine hydrothermal systems (Fiala, G. & Stetter, K. O.; Arch. Microbiol., 145, 56–61 (1986) and Kelly, R. M. & Deming, J. W., Biotech. Progress, 4, 47–62 (1988). The most extreme thermophilic bacteria known so far belong to the genera Pyrococcus, Pyrodictium and Pyrobaculum. It has been presumed that members of Pyrococcus contain heat stable proteases and amylases (Stetter, K. O., J. Chem. Technol. Biotechnol., 42(4); 315–317 (1988)). Growth conditions for *Pyrococcus woesei* have been examined (Zillig et al.; Syst. Appl. Microbiol., 9, 62–70 (1987)). However, amylases from Pyrococcus have never been isolated or investigated.

In order to eliminate the need for intermediate pH adjustment the art has long sought for thermostable starch liquefaction enzymes capable of liquefying at pH as low as 4.0. Moreover it is preferred to avoid addition of calcium salts in order to reduce purification costs. Therefore it is an object of the present invention to obviate the shortcomings of the α-amylases known heretofore by furnishing a novel hyperthermostable α-amylase that has a low pH optimum, and that is essentially independent of calcium ions.

BRIEF DISCLOSURE OF THE INVENTION

It has now according to the present invention been found that strains of Pyrococcus produces α-amylases which, in addition to an extraordinary thermostability, exhibit pH optima at favourably low pH values and are essentially independent of calcium ions.

According to its first aspect, the present invention provides an α-amylase having pH optimum within the range 4.0 to 6.0, determined at 90° C. in presence of stabilizing amounts of substrate, temperature optimum within the range 80° to 120° C., determined at pH 5.5 in presence of stabilizing amounts of substrate, being essentially independent of Calcium ions, and having a residual activity after 1 hour at 90° C. of 100%, and after 1 hour at 100° C. of at least 80%, determined in presence of stabilizing amounts of substrate. In another variant of this aspect, the invention provides an α-amylase having pH optimum within the range 5.2–5.8, determined at 90° C. in absence of substrate, temperature optimum within the range 90°–105° C., determined at pH 5.5 in absence of substrate, being independent of Ca-ions, and having a residual activity after 1 hour at 110° C. of approximately 70%, determined in presence of stabilizing amounts of substrate.

The α-amylase according to the invention is obtainable by cultivation of a strain of Pyrococcus. Preferred strains are *P. woesei* and *P. furiosus*, particularly *P. woesei*, DSM No. 3773, and *P. furiosus*, DSM No. 3638.

In a second aspect, the invention provides a process for the preparation of these α-amylases, comprising cultivation of an α-amylase producing strain of Pyrococcus in a suitable nutrient medium containing carbon and nitrogen sources and inorganic salts, followed by recovery of the desired enzyme. In preferred embodiments of this process a strain of *P. woesei* or *P. furiosus* is cultivated, particularly *P. woesei*, DSM No. 3773, or *P. furiosus*, DSM No. 3638.

In a third aspect, the invention provides a starch liquefaction process, which comprises subjecting an aqueous starch slurry to enzymatic liquefaction, in the presence of an α-amylase according to the invention. In a preferred embodiment of this process, the starch liquefaction is carried out essentially without addition of a calcium salt to the starch slurry. In a further preferred embodiment, the process is conducted by jet-cooking at a temperature in the range 100°-140° C. for up to 120 minutes, optionally followed by reduction of the temperature to be held in the range 90°-100° C. for about 30 to 120 minutes, after which the thus liquefied starch is stable against retrogradation, the pH being held at about 4.0 to 5.5 throughout the process. In another preferred embodiment of the present invention, the liquefied starch is thereafter subjected to enzymatic saccharification in the presence of glucoamylase, substantially without an intermediate pH adjustment. In yet another preferred embodiment of this invention, the liquefied starch is further subjected to ethanol fermentation with yeast simultaneously with or subsequent to saccharification.

DETAILED DISCLOSURE OF THE INVENTION

Growth experiments with Pyrococcus have now shown that members of this genus secrete a most thermostable and thermoactive starch hydrolysing enzyme ever described. These starch degrading enzymes are capable of hydrolysing at random the α-1,4-glycosidic linkage in various glucose polymers such as e.g. amylopectin, glycogen, maltodextrin and amylose. From the pattern of polysaccharide hydrolysis these enzymes are identified as α-amylases.

At present two species of Pyrococcus are known, *P. woesei* and *P. furiosus*. The α-amylases produced by these organisms apparently possess similar properties, although they might be slightly different in structure. A strain of *P. woesei* is available from DSM, with No. 3773. A strain of *P. furiosus* is available from DSM, with No. 3638.

The enzymes of the invention are stabilized by their substrate, i.e. the presence of polysaccharides such as e.g. starch, glycogen, branched or linear glucosepolymers, amylose, amylopectin, maltodextrin, or mixtures hereof, and they are stable in absence of metal ions. The stabilizing effect of the substrate occurs at polysaccharide concentrations of approximately 0.5% or more (by weight). Minor polysaccharide concentrations do not bring about stabilization.

The enzymes of the invention display temperature optimum at 80° to 120° C. and are active from 40° C. to 140° C., especially between 60° and 120° C., more particularly between 80° and 110° C., and most particularly between 90° and 105° C. This broad temperature range of 100 degrees is amazing. The enzymes are catalytically active within pH 3.5 to 8.0. Around 60% of activity is measured at pH 3.5 and 7.0. The pH optimum for the enzymatic activity is within pH 4.0 to 6.0, more particularly between pH 4.0 to 5.5 when determined in a medium containing stabilizing amounts of polysaccharides, and within pH 5.2 to 5.8 when determined in absence of stabilizing amounts of polysaccharides.

The extraordinary properties of the enzymes of the invention were demonstrated by detection of enzymatic activity even after autoclaving for 6 hours at 120° C. at a pressure of 3 bar. Almost 20% of α-amylase activity was detected even at 120° C. After 60 minutes a residual activity of 100% at 90° C., at least 80% at 100° C., approximately 70% at 110° C., and at least 60% at 120° C. is measured. For the complete inactivation of the α-amylase at least 12 hours of autoclaving at 120° C. at pressure of 3 bars was necessary. It is also remarkable, that the enzyme is catalytically active after boiling in the presence of detergents such as 2% SDS.

Further in vitro studies have shown that metal ions or other intracellular factors are not needed for the catalytic activity of the purified enzyme. The addition of 1 to 5 mM of heavy metals such as $Cr^{2+}$, $Cu^{2+}$ or $Zn^{2+}$ caused enzyme inhibition. This inhibition could be elevated by the addition of 5 mM of EDTA.

The unique properties of the α-amylases according to the present invention allow their utilization in existing commercial processes and novel applications. The unique thermostability and the ability to convert native starch as well as soluble starch, in the absence of metal ions, at pH values below 5 and at temperatures above 100° C., to a mixture of saccharides, makes these enzymes ideally suited for industrial starch liquefaction, e.g. for the production of fuel alcohol or High Fructose Syrup (HFS). The use of these enzymes in starch liquefaction processes, is thus accomplished by extraordinary process-technical advantages. It is not necessary to readjust the pH-level between the two steps liquefaction and saccharification. The formation of unwanted by-products is avoided. It is not necessary to add calcium in order to stabilize the enzyme, and accordingly operating costs for ion exchange purification can be reduced significantly. Due to a higher temperature, the reaction proceeds faster.

Preparation of α-Amylase

α-amylases according to the invention can be prepared by cultivating a strain of Pyrococcus in a suitable growth medium and thus harvesting the produced enzyme.

Pyrococcus exhibits growth maximum at 80° to 106° C., with the upper temperature limit around 110° C., and at pH values between 4.5 and 7.5. The enzyme synthesis of the organism occurs any time during growth and starts already in the early logarithmic phase and reaches its optimum during the stationary phase. From a large number of protein bands detected, using polyacrylamide gradient gel electrophoresis, only one major band displays amylolytic activity. The molecule weight of this enzyme is approximately 70 KDa.

As earlier mentioned, growth conditions for *P. woesei* have been examined, and a method for cultivation is described (Zillig et al., supra). In order to obtain a fermentation method with better industrial applications, a process for the preparation of an α-amylase according to the invention has been developed that accomplish continuous gassing of the nutrient medium. It was found that continuous gassing of the nutrient medium stimulates the enzyme production. It appears that the extracellular enzyme level increases about two fold. By continuous gassing with a $H_2/CO_2$-atmosphere and with saccharides such as e.g. starch, amylose, amylopectin, glycogen, branched or linear oligosaccharides and maltodextrin, or mixtures thereof as a carbon source, elementary sulphur as an electron acceptor and 3% NaCl, 220 U/l α-amylase are secreted into the medium. Under non-continuous gassing only 120 U/l α-amylase can be detected under the same conditions.

In addition a more defined nutrient medium for the growth of Pyrococcus has been developed. Unlike other media described, this medium is not turbid, and it does not contain elementary sulphur. Good growth and enzyme production in this medium can be obtained by continuous gassing with $N_2/CO_2$. With this nutrient medium the enzyme production is further elevated up to 5 folds from about 200 U/l to above 1,000 U/l of the extracellular enzyme. The composition of this medium appears from example 2. Interestingly, we could also show that if cultures were only gassed with nitrogen, growth and enzyme production were lowered. Since this medium is not turbid, growth can now easily be monitored by measuring the optical density. The organism also secretes a comparable amount of enzyme. The above mentioned media (with and without sulphur) are used for the production of amylase in small as well as in large amounts.

The α-amylases according to the present invention may also be prepared by recombinant DNA-technology.

Isolation of α-amylases

The isolation of α-amylases according to the invention can be accomplished by conventional means. The enzyme can easily be recovered from the cell-free supernatant. They adsorb to native and soluble starches which allow the purification of these enzymes on a large scale. However, stabilization of the α-amylase with 0.5% maltodextrin is required. They can be precipitated from the supernatant by cold or addition of organic solvents such as ethanol, which does not reduce the activity of the enzyme.

Starch liquefaction process

The liquefaction process of the invention may be used for enzymatic conversion of starch into sugars, e.g. for the production of fuel alcohol or High Fructose Syrup (HFS). Suitable liquefaction conditions are up to 120 minutes at 100° to 140° C., more preferred 1 to 60 minutes at 100° to 120° C., most preferred 1 to 30 minutes at 105° to 110° C., optionally followed by reduction of the temperature to be held in the range of 90° to 100° C. for about 30 to 120 minutes. It is preferred not to add calcium salts to the aqueous starch slurry. The pH should be held within 3.5 to 6.0, more preferred 4.0 to 5.5, most preferred 4.2 to 4.8. A continuous process is preferred, and the heating is most preferably by jet-cooking. The α-amylase of the invention liquefies starch well at dosage levels of 5–500 NU (see below for the definition of NU), preferably 10–50 NU, per gram starch DS (dry substance). The starch concentration will usually be in the range 15–45% DS (w/w% dry substance), most often 25–35% DS.

The liquefied starch may hereafter be subjected to enzymatic saccharification in the presence of a glucoamylase, substantially without an intermediate pH adjustment. In this case the starch is liquefied with α-amylase of this invention at pH 3.5–6.0, more preferred at pH 4.0–4.5, most preferred pH 4.2–4.8. The liquefied starch may also be subjected to subsequent enzymatic saccharification in the presence of a glucoamylase in combination with a debranching enzyme such as pullulanase (see EP 63.909 for details) and/or an acid stable α-amylase from for example *A. niger* ( see EP 140.410 for details) .

The liquefaction process of the invention may also be used for producing ethanol. In this case the starch is liquefied with α-amylase at a pH of 3.5–6.0, more preferred 4.0–5.5, followed by saccharification with glucoamylase and simultaneous or subsequent fermentation with yeast. Thereafter the alcohol may be recovered by methods known in the art. Preferably the whole process is carried out at pH around 4.5 without any intermediate pH adjustment, and simultaneous saccharification and fermentation is performed at 30°–35° C. for up to 96 hours. The liquefaction can be conducted either at low DS levels (15–20%) or high DS levels (20–40%). In the high DS processes, the DS level must be reduced to about 20% prior to fermentation to obtain about 10% alcohol by volume, which is about maximum that most yeast can tolerate.

The raw material for alcohol production may include refined starch such as wet milled corn starch; raw, unprocessed materials such as corn, wheat, rice, sorghum, cassawa and potato (whose starch content range from 15 to 80%); and other starch containing materials such as waste and by-products from industry.

BRIEF DESCRIPTION OF DRAWINGS

FIG. 1: Cultivation of *P. woesei* in a continuously gassed batch culture on starch at 98° C. (● amylase activity; △ residual starch; ■ pH; ◇ optical density at 578 nm).

Figure 2A:
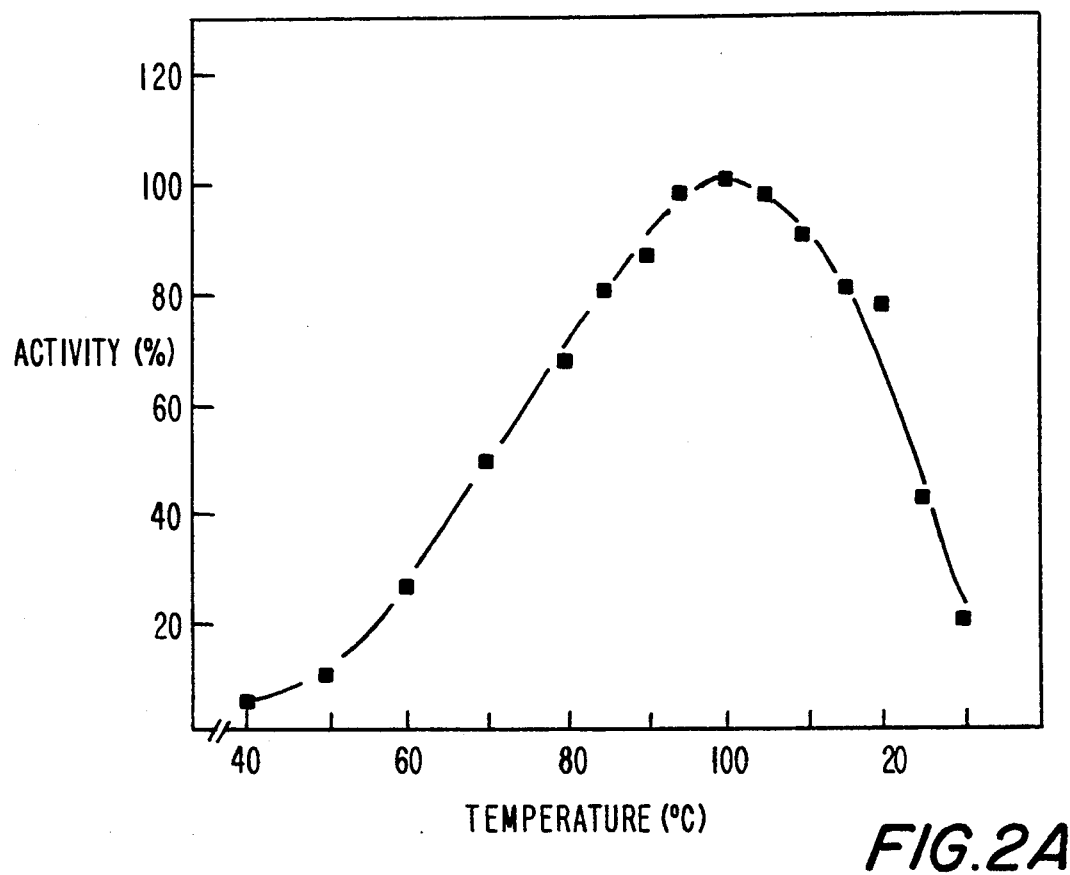
FIG. 2: The influence of temperature and pH on the activity of α-amylase from *P. woesei*.

The following examples further illustrates the present invention.

EXAMPLE 1

α-Amylase Obtained from *P. woesei*

Cultivation of *P. woesei* (Compare FIG. 1)

*Pyrococcus woesei* was cultivated in a medium as described by Zillig et al. (supra) at 98° C. 20 l cultures were continuously gassed with $H_2/CO_2$ 80:20 and 50 ml samples were withdrawn after various time intervals. Amylase activity was determined in the cell-free supernatant according to Bergmeyer and Grassi, Methods of enzymatic analysis, 3rd ed., Vol. 2, 151–152; Verlag Chemie, Weinheim (1983). To 250 μl of sodium acetate buffer (50mM pH 5.5) containing 1% (w/v) starch, up to 100 μl of enzyme solution was added and incubation was conducted at 95° C. for 30 and 60 min. The activity of 1 U of α-amylase is defined as that amount of enzyme which liberates 1 μmol of reducing sugar per min with maltose as a standard. Residual starch concentration was estimated employing HPLC as described in Table 1.

TABLE 1

| | Sugars released (%) by the enzymic action of α-amylase from *Pyrococcus woesei* on starch. | | | | | | | |
|---|---|---|---|---|---|---|---|---|
| Time | DPn | DP7 | DP6 | DP5 | DP4 | DP3 | DP2 | DP1 |
| 0 h | 100 | 0 | 0 | 0 | 0 | 0 | 0 | 0 |
| 4.5 h | 84 | 3 | 3 | 2 | 2 | 3 | 3 | 0 |
| 7.0 h | 71 | 4 | 4 | 2 | 4 | 7 | 8 | 0 |
| 12.5 h | 57 | 6 | 7 | 3 | 5 | 10 | 12 | 0 |
| 23.5 h | 35 | 14 | 16 | 5 | 6 | 11 | 13 | 0 |

TABLE 1-continued

| | Sugars released (%) by the enzymic action of α-amylase from *Pyrococcus woesei* on starch. | | | | | | | |
|---|---|---|---|---|---|---|---|---|
| Time | DPn | DP7 | DP6 | DP5 | DP4 | DP3 | DP2 | DP1 |
| 35.5 h | 29 | 13 | 17 | 5 | 7 | 12 | 16 | 1 |

Methods: Per ml of sodium acetate buffer (50 mM, pH 5.5) 0.5 U of enzyme was added. The final starch concentration was 1% (w/v). Incubation was conducted at 90° C. and samples were withdrawn after various time intervals. Each sample was then purified with ion-exchange resin (Serdolyt MB, Serva, Heidelberg, FRG) and the sugars then analyzed by HPLC, using an Aminex HPX-42 A column (Bio-Rad, Richmond, Calif., USA). Sugars eluted were monitored by a differential refractometer (Knauer, Bad Homburg, FRG), DP, Degree of polymerization; DP 1, glucose.

Protein Separation

Figure 2B:
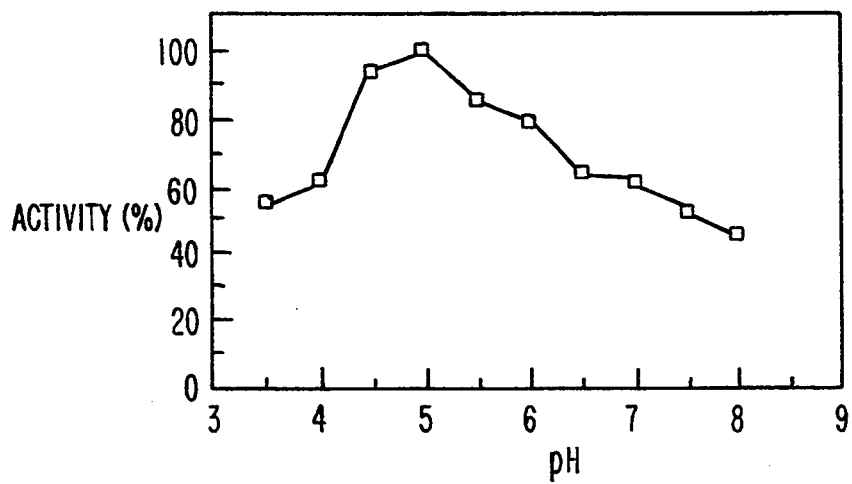

The separation of the extracellular proteins (20 μg, 0.2 U) was performed in 1.5 mm thick polyacrylamide gradient gels (5 to 30%, w/v) at a constant voltage of 400 v for 24 h at 4° C. For the detection of protein band exhibiting amylase activity the gel was soaked in 50 mM acetate buffer, pH 5.5 containing 1% starch for 1 h at 4° C. The gel was further incubated at 90° C. for 30 min. and finally incubated in a solution containing 0.15% (w/v) iodine and 1.5% (w/v) potassium iodide until clear zone became visible. The proteins in the same gel were silver stained according to Heukeshoven and Dernick, Electrophoresis 6, 103–112. Standard proteins (10 μg of each) with known molecular mass were also separated. The molecule weight of the protein, that show amylolytic activity, is approximately 70 KDa.

pH and Temperature Optimum (Compare FIG. 2)

Determination of temperature optimum was performed with enzyme which was partially purified by gel filtration on a Superose 12 column and stabilized with 0.5% maltodextrin. Incubation was performed in a water bath (40° C.–100° C.) and in a glycerin bath (105° C.–130° C.), at pH 5.5. Incubation at temperatures above 100° C. was conducted in closed Hungate-tubes in order to prevent boiling of the solution. To 250 μl of a sodium acetate buffer (50 mM, pH 5.5), containing 0.5% (w/v) starch, 20 μl of enzyme solution (1600 U/l) was added and incubation was performed for 10 minutes. The reducing sugars formed were then measured as described by Bergmeyer and Grassi (supra). For the determination of the pH optimum of the enzyme the following buffers were used: 50mM sodium citrate (for pH 3.5–4.0), 50 mM sodium acetate (for pH 4.5–6.0) and 50 mM potassium phosphate (for pH 6.5–8.0). The pH determination was conducted at 90° C.

The tested enzyme is active in a broad temperature range from 40° to 130° C. and a pH range 3.5 to 8.0. Maximal activity is detected at pH 5 and 100° C.

Figure 3:
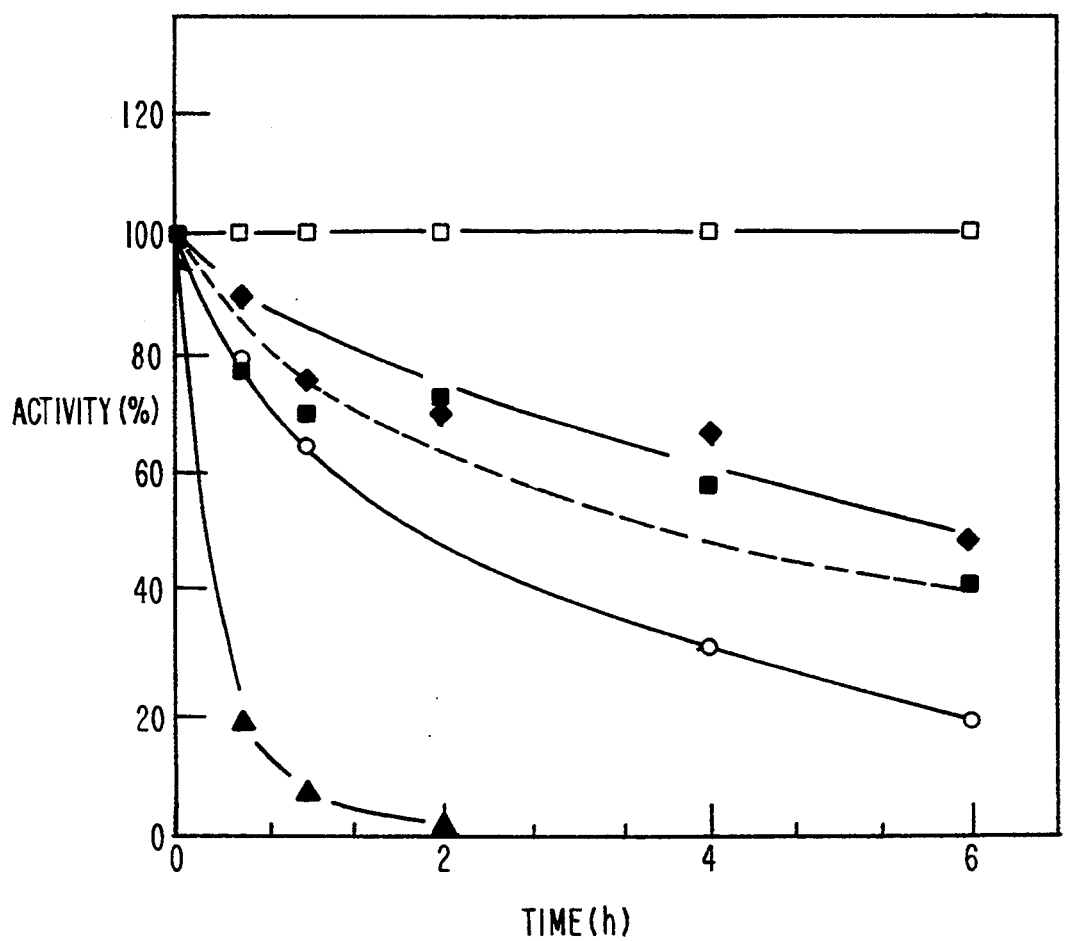
FIG. 3: Thermal stability of α-amylase from *P. woesei* (□ 70°–90° C.; ◆ 100° C.; ■ 110° C.; ○ 120° C; ▲ 130° C.).

Thermal Stability (Compare FIG. 3)

The sample containing the enzyme was incubated in water (70°–90° C. and glycerin bath (100°–130° C.). After various time intervals samples were withdrawn and the α-amylase activity was determined according to Bergmeyer and Grassi (supra). To 200 μl sodium acetate buffer (50 mM, pH 5.5) containing 1% (w/v) starch, up to 50 μl of enzyme solution was added and incubation was conducted for 30 and 60 min. at 95° C. (□ 70°–90° C.; ◆ 100° C.; ■ 110° C.; ○ 120° C; ▲ 130° C.).

The Influence of Metal Cations and EDTA

The influence of metal cations and EDTA on the activity of α-amylase from *P. woesei* was performed with enzyme which was partially purified by gelfiltration on a Supsrose 12 column (Pharmacia, Sweden), see Table 2. The fractions containing α-amylase were collected and concentrated 4-fold. 25 μl of enzyme (400 U/l) were added to 100 μl of sodium acetate buffer (50 mM, pH 5.5) containing 1% (w/v) starch. Metal cations, which were dissolved in sodium acetate buffer (100 mM, pH 5.5), were added in various concentrations. Incubation was conducted in a glycerin bath (100° C.) for 40 min. The reducing sugars were finally detected as described by Bergmeyer and Grassi (supra). The values represent the enzyme activity measured in percent.

TABLE 2

| Metal ion | 0 | concentration (mM) | | |
|---|---|---|---|---|
| | | 1 | 2 | 5 |
| EDTA | 100 | 95 | 85 | 60 |
| $Ca^{2+}$ | 100 | 120 | 120 | 85 |
| $Co^{2+}$ | 100 | 120 | 100 | 80 |
| $Cr^{2+}$ | 100 | 6 | 2 | 1 |
| $Cu^{2+}$ | 100 | 6 | 2 | 0 |
| $Fe^{2+}$ | 100 | 80 | 55 | 15 |
| $Mg^{2+}$ | 100 | 95 | 85 | 110 |
| $Mo^{2+}$ | 100 | 105 | 100 | 120 |
| $Ni^{2+}$ | 100 | 70 | 65 | 50 |
| $Zn^{2+}$ | 100 | 15 | 0 | 0 |

EXAMPLE 2

α-Amylase Obtained from *P. furiosus*

Figure 4A:
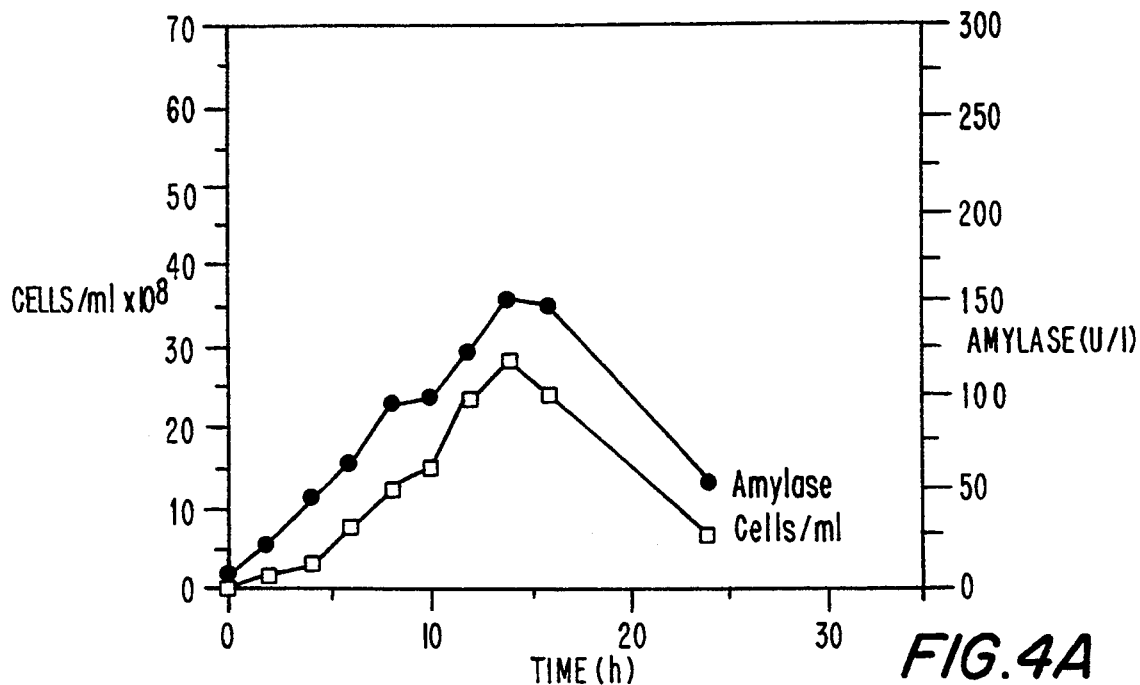
FIG. 4: (A) Secretion of α-amylase by *P. furiosus* during growth on starch at 98° C. (B) Growth under continuous gassing.
Figure 4B:
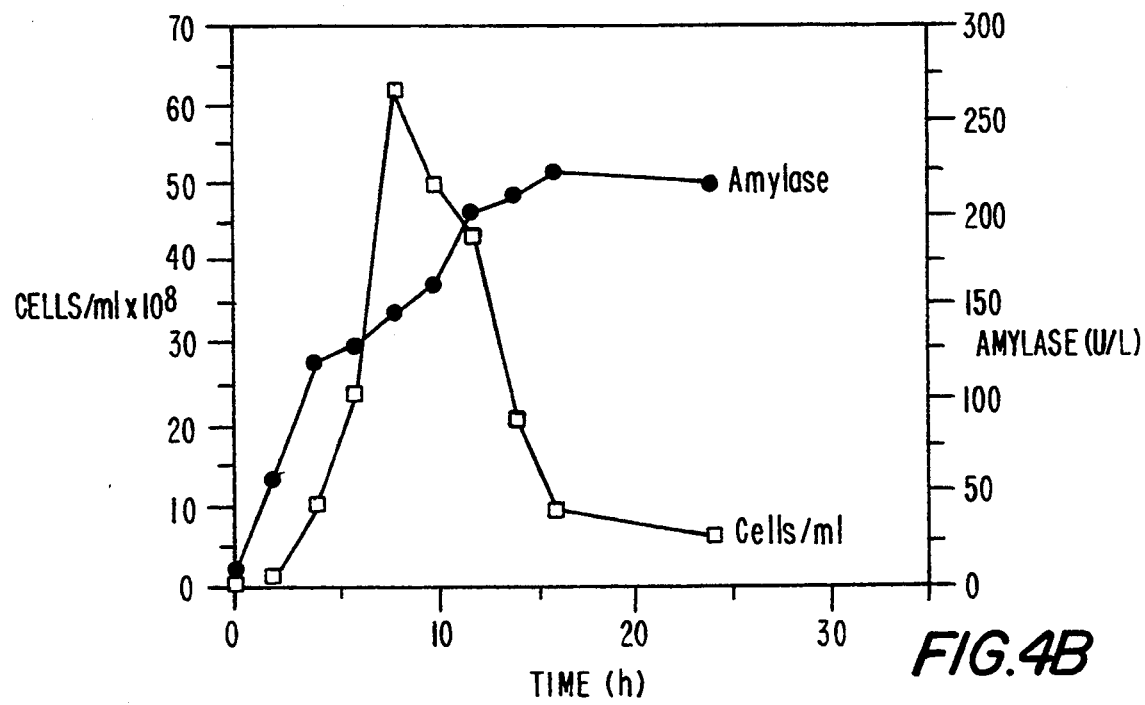

Cultivation of *P. furiosus* (Compare FIG. 4)

Growth experiments were performed in batch-culture under $N_2/CO_2$ (80%/20%) atmosphere on a complex medium of the following composition (per liter):

$(NH_4)_2SO_4$: 1.300 g
$MgSO_4.7H_2O$: 0.250 g
NaCl: 30.000 g
$KH_2PO_4$: 1.400 g
$CaCl_2$: 0.050 g
$FeSO_4.7H_2O$: 0.038 g
$Na_2SeO_3.5H_2O$: 5 μM
trace elements**: 10 ml
tryptone: 1.000 g
yeast extract: 1.000 g
starch: 1.000 g
resazurin: 0.001 g
cystein.HCl: 0.500 g
pH 6.2–6.5
temperature 90°–100° C.
Gas $N_2/CO_2$ 80/20 (continuous gassing)
**trace element solution (per liter):
$MnCl_2.4H_2O$: 0.10 g
$CoCl_2.6H_2O$: 0.20 g
$NiCl_2.6H_2O$: 0.10 g
$ZnCl_2$: 0.10 g
$CaCl_2.2H_2O$: 0.05 g
$CuSO_4.2H_2O$: 0.05 g
$NaMoO_4.2H_2O$: 0.05 g By using continuous gassing an enzyme activity above 1,000 U/l was detected. These growth conditions caused about 80% secretion of the enzyme into the culture fluid.

Protein Separation

In order to conduct physiochemical investigations the extracellular amylase was partially purified by gel-filtration. All experiments were performed in the absence of metal ions and under aerobic conditions.

Figure 5A:
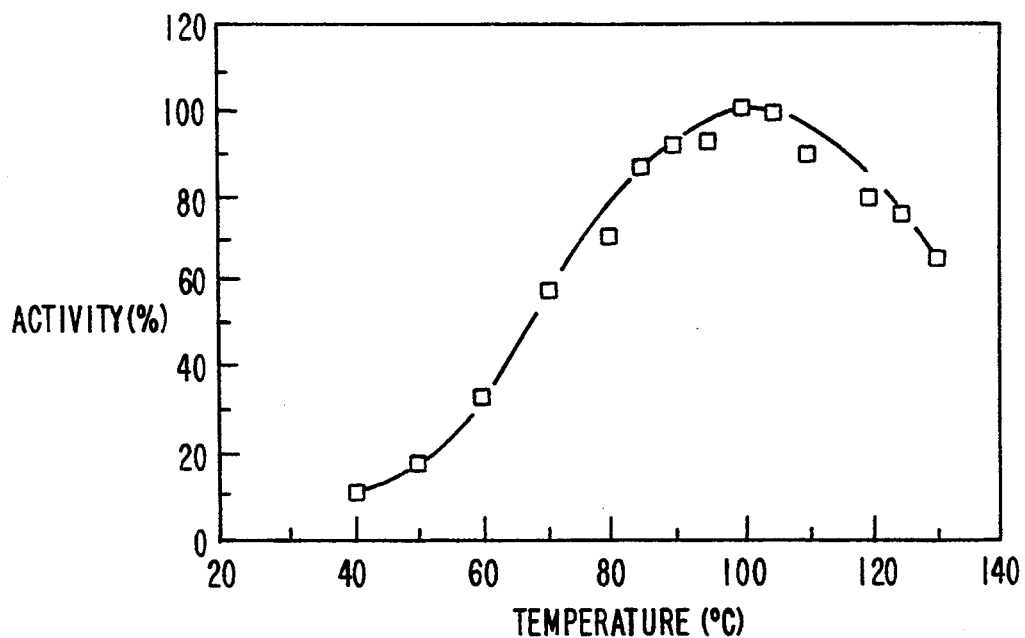
FIG. 5: The influence of temperature and pH on the activity of α-amylase from *P. furiosus*.
Figure 5B:
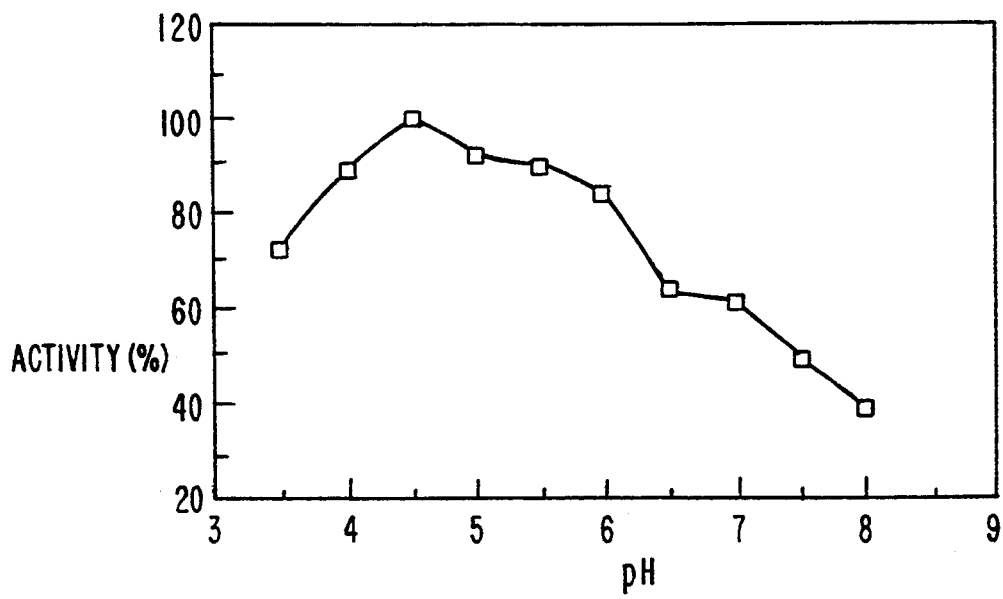

PH and Temperature Optimum (Compare FIG. 5)

As shown in the figure, the amylase from *Pyrococcus furiosus* is active in a broad temperature range from 40° to 130° C. and in a pH range from 3.5 to 8.0. Maximal activity is measured at 100°–105° C. and pH 4.5. Around 60% of the enzyme activity is still detectable at 130° C. Conditions incubation of *Pyrococcus furiosus* α-amylase, for the determination of pH and temperature optimum, were as for *Pyrococcus woesei* α-amylase.

Figure 6:
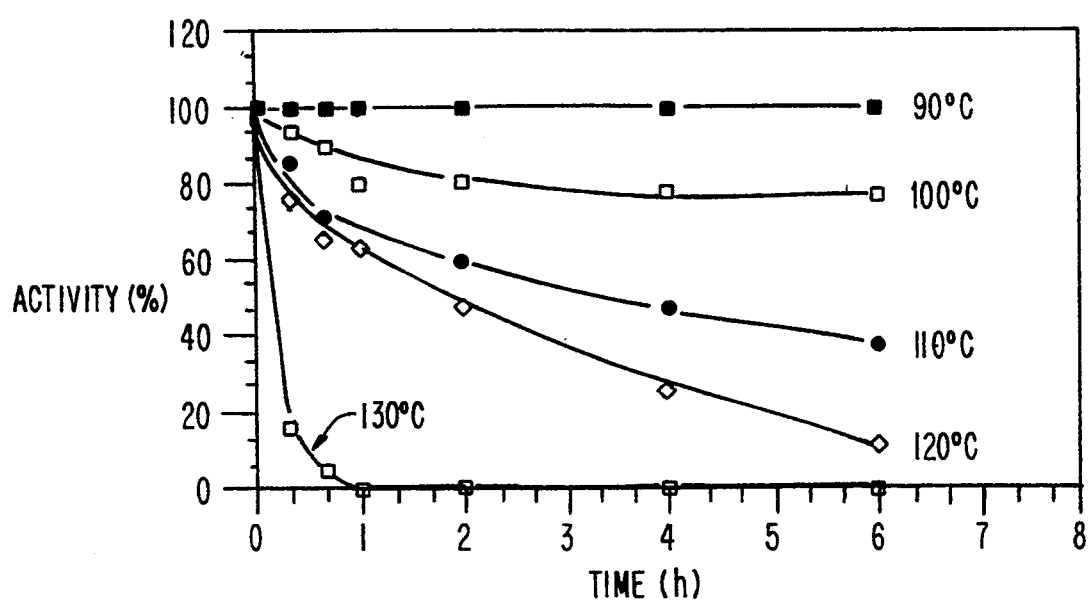
FIG. 6: Thermal stability of α-amylase from *P. furiosus*.

Thermal Stability (Compare FIG. 6)

Besides the extremely high temperature optimum, the amylase shows remarkable thermal stability. As depicted in the figure, incubation in a boiling water bath for 6 hours causes a decrease of enzymatic activity of only 20%. Even at 130° C. enzymatic activity is still detectable after 30 minutes.

Influence of Metal Ions and EDTA

The addition of 5 mM of molybdenum, calcium or magnesium ions did not influence amylase activity. A slight decrease of activity could be detected in the presence of cobalt, nickel and iron ions and complete inhibition was found when 5 mM of zinc or copper ions were added. Since EDTA did not have any influence, it, therefore, can be assumed that the addition of metal ions is not required for enzymatic activity.

Substrate Specificity

The partially purified extracellular amylase from *Pyrococcus furiosus* hydrolysed native starch, soluble starch, amylopectin, maltodextrin and amylose. Main products of starch degradation were oligosaccharides such as maltohexaose, maltopentaose, maltotetraose, maltotriose and maltose (Table 3). Since the amylase from Pyrococcus furiosus degrades the α-1,4-glycosidic linkages in starch and amylase at random it can be designated as an α-amylase.

TABLE 3

Sugars released (%) by the enzymic action of amylase from *Pyrococcus furiosus* during incubation with starch.

| Starch | DPn | DP7 | DP6 | DP5 | DP4 | DP3 | DP2 | DP1 |
| --- | --- | --- | --- | --- | --- | --- | --- | --- |
| 0 h | 100 | 0 | 0 | 0 | 0 | 0 | 0 | 0 |
| 0.5 h | 93 | 1 | 1 | 1 | 1 | 1 | 2 | 0 |
| 1.5 h | 41 | 4 | 6 | 10 | 11 | 11 | 12 | 5 |
| 3 0 h | 35 | 8 | 9 | 11 | 10 | 10 | 12 | 5 |
| 8.0 h | 1 | 4 | 6 | 15 | 19 | 21 | 27 | 8 |
| 24.0 h | 0 | 2 | 2 | 6 | 16 | 25 | 33 | 16 |
| 48.0 h | 0 | 0 | 3 | 6 | 12 | 20 | 30 | 29 |

Methods: Per ml of sodium acetate buffer (50 mM, pH 5.5) 0.5 U of enzyme was added. The final starch concentration was 1% (w/v). Incubation was conducted at 90° C. and samples were withdrawn after various time intervals. Each sample was then purified with ion-exchange resin (Serdolyt MB, Serra, Heidelberg, FRG) and the sugars then analyzed by HPLC, using an Aminex HPX-42 A column (Bio-Rad, Richmond, Calif., USA). Sugars eluted were monitored by a differential refractometer (Knauer, Bad Homburg, FRG). DP, Degree of polymerization; DP 1, glucose.

EXAMPLE 3

Liquefaction Process

A 30% w/w corn starch slurry was prepared in deionized water and the pH adjusted to 4.5. It was then transferred to a stainless steel tube, equipped with a tight-fitting lid, and 17 NU/g starch of *P. woesei* α-amylase were added.

The tube was heated at 105° C. for 60 minutes, during which the starch was completely liquefied. After liquefaction the DE was measured and found to be 16.

The contents of the tube were cooled to 60° C., and 0.24 AG/g starch of *A. niger* glucoamylase was added without further pH adjustment. After 72 hours the sample had the following carbohydrate composition, as measured by HPLC analysis:

%$DP_1$: 95.5
%$DP_2$: 3.0
%$DP_3$: 0.9
%$DP_4$: 0.5 where DP means degree of polymerization ($DP_1$=monosaccharides, $DP_2$=disaccharides etc.).

Assay of α-Amylase Activity

The activity standard NU (which is an abbreviation of NOVO α-amylase unit) is the amount of enzyme which hydrolyses 5.26 mg of dissolved starch per hour at 37° C., pH 5.6 and 0.0043 M of $Ca^{++}$ over a 7–20 minute reaction time. A folder AF9 describing the analytical method is available on request to NOVO NORDISK A/S, DENMARK.

The activity of the Pyrococcus α-amylase is determined at 60° C. and related to a Termamyl standard, assayed under the same conditions.

EXAMPLE 4

Characterisation of Unstabilized α-Amylase

Figure 7A:
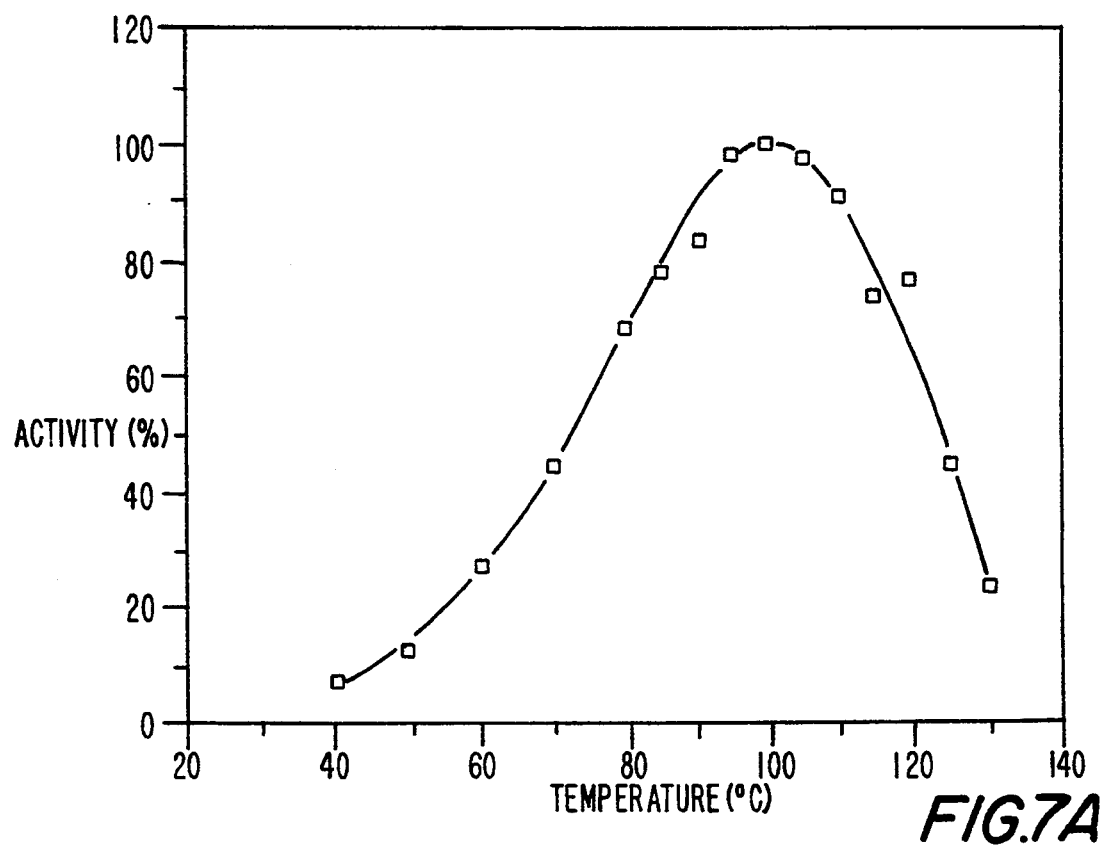
FIG. 7: The influence of temperature and pH on the activity of unstabilized α-amylase from *P. woesei*, determined in absence of substrate.
Figure 7B:
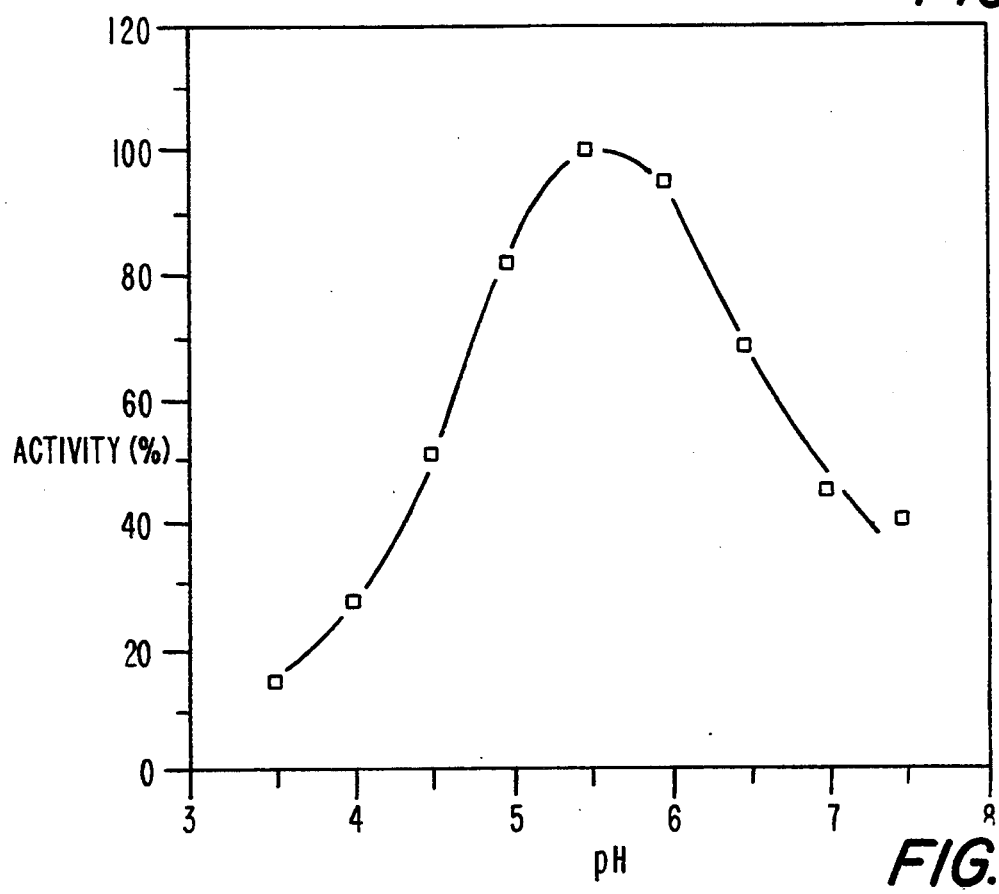

PH and Temperature Optimum (Compare FIG. 7)

Determination of temperature optimum was performed with the enzyme obtained in example 1, which was partially purified by gelfiltration on a Superose 12 column, but not stabilized with maltodextrin. Incubation was performed in a water bath (40° C.–100° C.) and in a glycerin bath (105° C.–130° C.), at pH 5.5. Incubation at temperatures above 100° C. was conducted in closed Hungate-tubes in order to prevent boiling of the solution. To 250 μl of a sodium acetate buffer (50 mM, pH 5.5) containing 0.5% (w/v) starch 20 μl of enzyme solution (1600 U/l) was added and incubation was performed for 10 minutes. The reducing sugars formed were then measured as described by Bergmeyer and Grassi (supra). For the determination of the pH optimum of the enzyme the following buffers were used: 50 mM sodium citrate (for pH 3.5–4.0), 50 mM sodium acetate (for pH 4.5–6.0) and 50 mM potassium phosphate (for pH 6.5–7.5). The determination was conducted at 90° C.

As shown in the figure, the α-amylase of the invention can also be characterised by having pH optimum in the range 5.2 to 5.8, determined at 90° C., and temperature optimum in the range 90° to 105° C., determined at pH 5.5, when measured in absence of stabilizing amount of substrate. Maximal activity is detected at pH 5.5 and 100° C.

After 60 minutes a residual activity at 100° C. of 100%, at 110° and 120° C. of 70%, and at 130° C. of 10% is measured.

What is claimed is:

1. An isolated α-amylase derived from *Pyrococcus woesei* or *Pyrococcus furiosus* having the following properties:

(a) a pH optimum between 4.0 and 6.0 at 90° C.;

(b) a temperature optimum between 80° and 120° C. at a pH of 5.5;

(c) an activity which is essentially independent of calcium ions; and (d) a residual activity of 100% after 1 hour at 90° C. and of at least 80% after 1 hour at 100° C. in the presence of stabilizing amounts of substrate.

2. The α-amylase according to claim 1 which is derived from *P. woesei* DSM No. 3773.

3. The α-amylase according to claim 1 which is derived from *P. furiosus* DSM No. 3638.

4. A process for preparing the α-amylase according to claim 1, comprising (a) cultivating an α-amylase producing strain of *Pyrococcus woesei* or *Pyrococcus furiosus* in a suitable nutrient medium containing carbon and nitrogen sources and inorganic salts and (b) recovering the desired enzyme.

5. The process according to claim 4, wherein said α-amylase producing strain is *P. woesei* DSM No. 3773.

6. The process according to claim 4, wherein said α-amylase producing strain is *P. furiosus* DSM No. 3638.

7. A process for producing a liquefied starch, comprising a liquefaction of a starch slurry in the presence of the α-amylase according to claim 1, wherein the liquefaction comprises:
(a) jet-cooking the starch slurry at a temperature between 100° and 140° C. for up to 120 minutes; and
(b) optionally reducing the temperature to between 90° and 100° C. for about 30 to 120 minutes;
wherein the pH is between 4.0 and 5.5 throughout the liquefaction.

8. The process according to claim 7, wherein the liquefaction is carried out without adding any calcium salt to the starch slurry.

9. A process according to claim 7, further comprising saccharification of the liquefied starch with a glucoamylase, without a pH adjustment after the liquefaction.

10. The process according to claim 9, further comprising ethanol fermentation with yeast simultaneously with or subsequent to said saccharification.

* * * * *